United States Patent [19]
DeLong

[11] Patent Number: 5,368,565
[45] Date of Patent: Nov. 29, 1994

[54] BALLOON CATHETER PRESSURE MONITOR FOR LOCAL AND REMOTE DISPLAY

[75] Inventor: Russell I. DeLong, Columbus, Ohio

[73] Assignee: Medex, Inc., Hilliard, Ohio

[21] Appl. No.: 952,915

[22] Filed: Sep. 28, 1992

[51] Int. Cl.⁵ ............................................ A61M 29/00
[52] U.S. Cl. .................................................. 604/100
[58] Field of Search ............................ 604/97-100, 604/67; 606/192, 194

[56] References Cited

U.S. PATENT DOCUMENTS

| | | |
|---|---|---|
| 3,698,381 | 10/1972 | Federico et al. |
| 3,893,452 | 7/1975 | Birnbaum |
| 3,985,123 | 10/1976 | Herzlinger et al. |
| 4,016,871 | 4/1977 | Schiff |
| 4,051,522 | 9/1977 | Healy et al. |
| 4,392,849 | 7/1983 | Petre et al. |
| 4,658,829 | 4/1987 | Wallace |
| 4,854,324 | 8/1989 | Hirschman et al. |
| 4,872,483 | 10/1989 | Shah |
| 4,877,035 | 10/1989 | Bogen et al. |
| 5,004,472 | 4/1991 | Wallace |
| 5,009,662 | 4/1991 | Wallace et al. |
| 5,021,046 | 6/1991 | Wallace |
| 5,084,060 | 1/1992 | Freund et al. |
| 5,135,488 | 8/1992 | Foote et al. |
| 5,215,523 | 6/1993 | Williams et al. .................. 604/97 |

FOREIGN PATENT DOCUMENTS

| | | |
|---|---|---|
| 8503007 | 7/1985 | WIPO . |
| 9207609 | 10/1991 | WIPO . |
| 9215361 | 4/1992 | WIPO . |

OTHER PUBLICATIONS

Intensive Patient Monitoring Systems Save Time and Labor in Hospitals, Hironami Kubota, Nihon Kohden Kogyo Co., Ltd., JEE, pp. 20-22 (Feb. 1976).
PCT International Search Report, PCT/US93/06021, dated Oct. 27, 1993, mailed Nov. 3, 1993.

Primary Examiner—C. Fred Rosenbaum
Assistant Examiner—Manuel Mendez
Attorney, Agent, or Firm—Wood, Herron & Evans

[57] ABSTRACT

Balloon catheter pressure monitor modules are provided with parallel connectors for daisy-chaining interchangeable modules such that pressure may be locally and remotely displayed and further for providing local and remote control of the processing circuitry of the modules.

25 Claims, 5 Drawing Sheets

BALLOON CATHETER PRESSURE MONITOR FOR LOCAL AND REMOTE DISPLAY

I. Field of the Invention

The present invention relates to balloon catheter pressure monitors such as are used to electronically display balloon pressure during an angioplasty procedure, for example.

II. Background of the Invention

Balloon catheter pressure monitors provide an electronic digital display of pressure in a balloon catheter such as used in an angioplasty procedure. As is well known, a typical angioplasty system includes a syringe coupled to a balloon catheter to be placed in a patient's blocked artery or the like. The balloon is inserted into an artery or vein and manipulated by a physician through the vascular system until the balloon is in the vicinity of the blockage. Fluid is then forced from the syringe into the balloon to inflate the balloon and compress the material blocking the artery against the walls of the artery to unblock the blood vessel. The balloon is then deflated and removed from the patient.

During the procedure, it is desirable to know the pressure in the balloon as well as to know the duration of balloon inflation. For this purpose, a monitor module is provided to digitally display both the pressure and the inflation duration for viewing by the doctor performing the procedure. To this end, a pressure transducer in fluid communication with the balloon catheter detects balloon pressure and generates electronic transducer signals corresponding to that pressure. A cable extending from the transducer carries the transducer signals into the module. For this purpose, the cable may be provided with a connector that plugs into a connector on the module such that the contacts of the two connectors are electrically interconnected. The transducer signals are communicated from the contacts to circuitry within the monitor module. The circuitry processes the transducer signals to produce numbers in units of pressure corresponding to the transducer signals which numbers are then displayed as the pressure in the balloon. Also, the onset of increased pressure above ambient is detected and a timer in the circuitry is initiated to display duration of the inflation. Various control elements may also be provided in the module, activation of which modifies operation of the circuitry. For example, a reset signal may be provided to reset the timer so that the duration display is reset to zero.

One such device is described in copending and commonly assigned application Ser. No. 07/932,645, filed Aug. 20, 1992, entitled "Electronically Monitored Angioplasty System", and the disclosure of which is incorporated by reference as if fully set out herein. Such a device allows the doctor performing the procedure to immediately see the pressure and duration and to control operation of the module, all on a local basis. Others not situated in the vicinity of the doctor, or not properly situated to view the display on the monitor module, may also need to know that same information or have control of the module, but do not have ready access to same. Thus, there is a need to also be able to produce a remote display of pressure and/or duration on a monitor module placed at a location removed from the doctor so that others needing that information will have ready access to it. While it might be possible to communicate the processed pressure number(s) and/or duration to a remote unit for display, such an approach introduces complexity to an already complicated procedure. Additionally, it is considered important that the two display devices (one at the doctor's location and the remote display) be interchangeable to avoid disruption or mistakes. Thus, it is desirable to use two similar or identical monitor modules.

SUMMARY OF THE INVENTION

The present invention provides a monitor module that not only receives the transducer signals for processing and display, but also reroutes the transducer signals to output contacts for communication over another cable to a second like monitor module for remote, simultaneous processing and display. Additionally, the various control signals, such as to reset the timer for example, may be exchanged over the interconnecting cable to thereby coordinate the local and remote modules. In this way, two interchangeable units may be daisy-chained together to provide local and remote display of pressure and/or duration based upon transducer signals provided by only one transducer and communicated over a cable interconnecting the modules. Further, control of both units, such as to simultaneously reset the duration displays of both units, may be accomplished by activating a reset button provided on either of the modules or on the syringe housing.

To these ends, and in accordance with the principles of the present invention, each monitor module is provided with a pair of connectors, respective contacts of which are connected together in parallel and to the circuitry within the module such that transducer signals communicated into the module via one of the connectors are coupled not only to the module circuitry for processing and display, but are also communicated back out through the other connector. A cable interconnecting that connector to another like module couples the rerouted transducer signals for duplicate processing and display by the remote module to thereby provide simultaneous local and remote display of pressure and/or duration.

Control signals, such as timer reset signals, are similarly communicated over the interconnecting cable such that resetting the timer in one of the modules will cause resetting of the timer in the other module as well. Other control signals may also be shared.

By virtue of the foregoing, there is thus provided a balloon catheter pressure monitor module adapted to be either a local display or a remote display, or part of a group of displays, with only one transducer being necessary to all of the displays and with the modules each being interchangeable.

These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the general description given above, and the detailed description given below, serve to explain the principles of the invention.

DETAILED DESCRIPTION OF THE DRAWINGS

Figure 1:
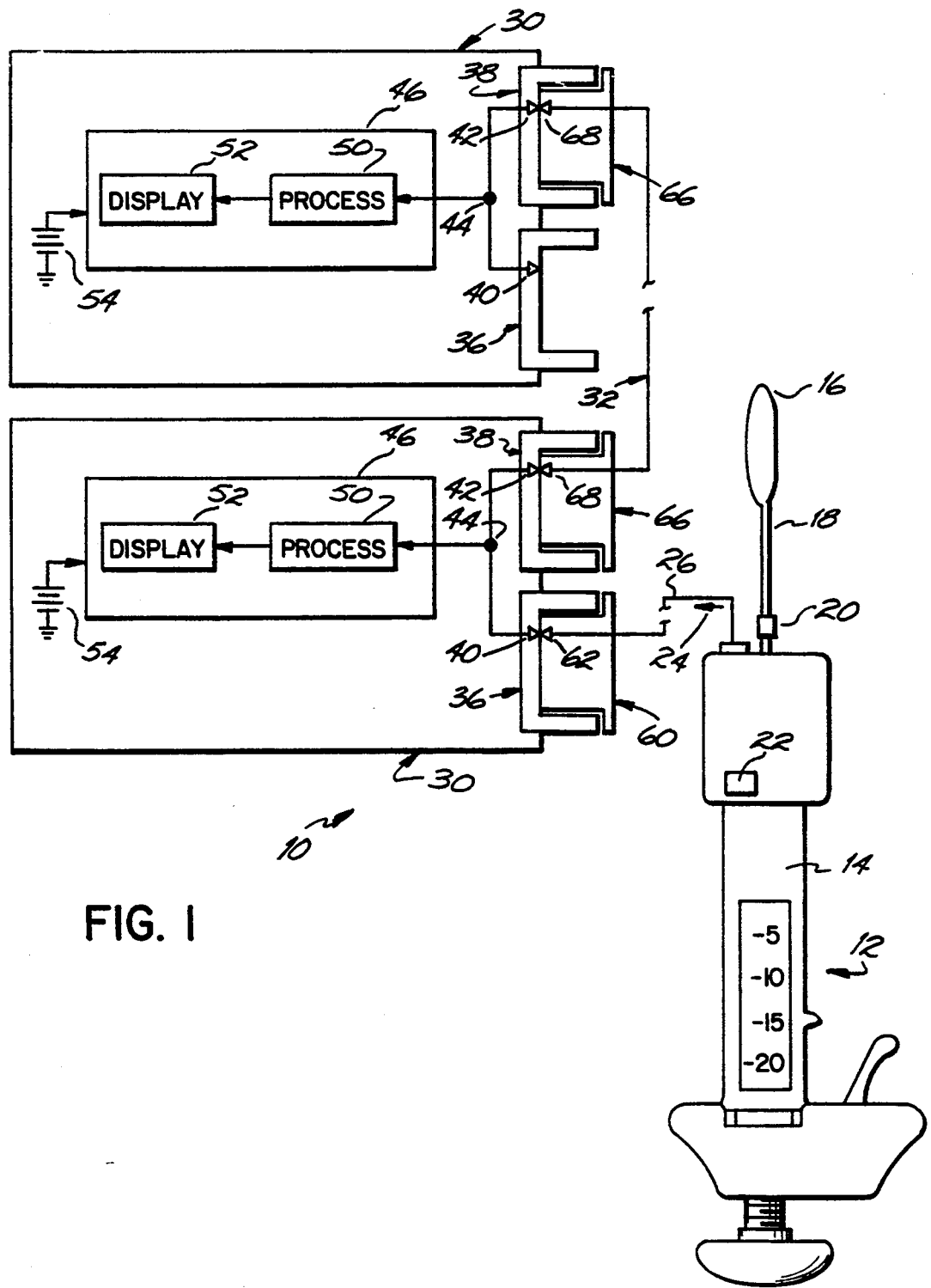
FIG. 1 is a simplified block diagram of one embodiment of a pair of balloon catheter pressure monitoring modules interconnected for local and remote display in accordance with the principles of the present invention.

With reference to FIG. 1, there is shown one embodiment of a local and remote electronic balloon catheter monitor system 10. System 10 includes angioplasty syringe 12 contained within housing 14 for inflating and deflating balloon 16 at the distal end of balloon catheter 18 coupled to outlet 20 of syringe 12. Mounted within housing 14 in fluid communication with syringe 12 and thus catheter 18 is electronic pressure transducer 22 for providing an electronic transducer signal 24 corresponding to the pressure in the catheter 18 and hence the balloon 16. Transducer signal 24 is coupled by cable 26 to a first or local, monitor module 30 and by interconnecting cable 32 to a second identical, but remotely positioned monitor module 30 for local and remote processing and display as will be described. As modules 30 are, in the embodiment of FIG. 1, identical, only one of them will be described.

Monitor modules 30 each include a pair of connectors 36, 38. Respective contacts 40 and 42 of connectors 36 and 38 are wired together in parallel as at 44 and further wired to circuitry 46. Signals are communicated between contacts 40 and 42 and circuitry 46 such that transducer signals 24 received at contacts 40 may be communicated both to the other module 30 through contacts 42 and to circuitry 46 for processing as at 50 to produce a number corresponding to the transducer signal. The number so produced is coupled to an electronic digital display or readout 52 for viewing by the user (not shown) of pressure in balloon 16 in units of pressure such as atmospheres (ATM) or PSI. Circuitry 46 may be powered by a 9-volt transistor battery 54 and may be turned on and off by an on/off switch (not shown).

To obtain the transducer signals, the end of cable 26 is provided with connector 60 formed to mate with connector 36 and having contacts 62 positioned to interconnect with contacts 40 when connector 60 is plugged into connector 36. Also, to connect the modules 30, interconnecting cable 32 is provided with distal connectors 66 each with contacts 68 to interconnect to the respective contacts 42 of connectors 38 when plugged into same.

In use, connector 60 of cable 26 is plugged into connector 36 of one of modules 30, and connectors 66 of cable 32 are connected to respective connectors 38 of each module 30. Thereafter, when syringe 12 is manipulated to inflate balloon 16, transducer 22 will generate transducer signals 24 that will be coupled over cable 26. The signals will also be coupled through contacts 40 of one module 30 so as to communicate transducer signals 24 from cable 26 to circuitry 46 of one module as well as to contacts 42 for communication through cable 32 to contacts 42 of connector 38 of remote module 30. In this way, transducer signals 24 are communicated to circuitry 46 in both modules 30 for local and remote processing and display.

Because transducer signals 24 are coupled to both modules 30 and because modules 30 are otherwise identical modules, they may be interchanged such that one may be placed in the vicinity of the doctor (not shown) performing the balloon catheter procedure for local viewing of the pressure on readout 52 and the other, interconnected by cable 32, may be placed in a remote location such as in a control room or lab for the monitoring of pressure on readout 52 of that remote module 30.

Connectors 36 and 60 may be conventional modular plugs and jacks as are used for telephones and connectors 38 and 66 may be conventional DIN connectors.

Figure 2:
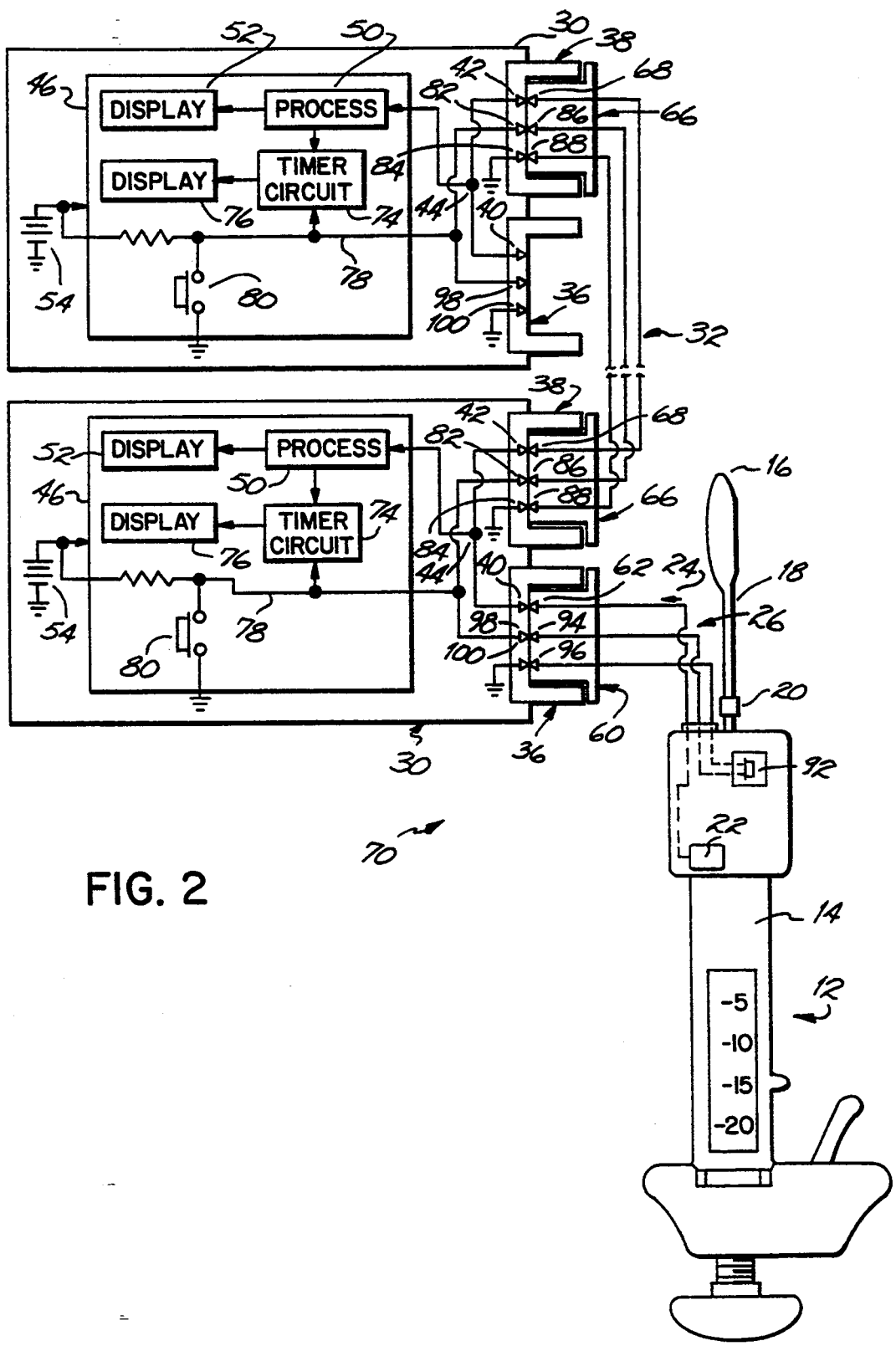
FIG. 2 is a simplified block diagram of a second embodiment of a pair of balloon catheter pressure monitor

With reference to FIG. 2, there is shown another embodiment of a local and remote electronic balloon catheter monitor system 70 which is similar to system 10 shown in FIG. 1 and further includes control of the processing circuitry to modify operation thereof. In the case of system 70, circuitry 46 includes timer circuitry for display of inflation duration which timer may be reset to cause the display to read zero as will now be described. To this end, local and remote modules 30 in system 70 further include within circuitry 46 a timer circuit 74 which begins counting on the onset of an increase in pressure within balloon 16 such that the output of timer circuit 74 provides a display on readout 76 of the duration of inflation. At the end of an inflation procedure, i.e., when the inflation in balloon 16 returns to ambient, timer circuit 74 will stop counting such that readout 76 will display the duration of the just-finished inflation and hold that display. Before beginning the next inflation of the balloon, it may be desirable to reset timer circuit 74 so that duration display 76 again reads zero. To this end, a reset signal may be provided to timer circuit 74 over line 78 to reset timer circuit 74. Line 78 is normally tied to a logical high, for example, but may temporarily be coupled to ground by activation of switch 80 on module 30 such that the temporary ground provides the reset signal. In order to provide for both local and remote control so that the timer circuit 74 of both modules 30 are reset together, connector 38 in each module is provided with contacts 82 and 84 connected to line 78 and ground, respectively, within each unit. Connectors 66 of interconnecting cable 32 are further provided with contacts 86, 88 to interconnect with respective contacts 82 and 84 of each module for communication of the reset signal between the modules. As a consequence, activation of switch 80 in either module 30 will reset timer circuit 74 in both modules.

Additionally, it may be desirable to allow for reset of timer circuits 74 by the doctor using syringe 12. To this end, switch 92 may be provided on syringe housing 14 with a pair of wires forming part of cable 26 extending therefrom and connected to contacts 94 and 96 of connector 60. Contacts 94 and 96 interconnect with contacts 98 and 100, respectively, of connector 36 with contacts 98 and 100 connected in parallel to contacts 82 and 84 of connector 38 and thus to line 78 and ground, respectively. Thus, activation of any reset switch 80 in either module 30 or the syringe reset switch 92 will cause a reset signal to be applied to timer circuit 74 in both modules to thereby reset duration display 76 in each module to zero. Modules 30 of system 70 are interchangeable to provide for local and remote display as well as for local and remote control of timer circuits.

In use of the embodiment of FIG. 2, connector 60 of cable 26 is plugged into a connector 36 and cable 32 connectors 66 are plugged into connectors 38. When balloon 16 is inflated, the transducer signals 24 are communicated simultaneously to both of modules 30 for processing and display of pressure at 52. Additionally, the onset of inflation pressure (represented by an increase in the magnitude of transducer signals 24, for example,) is detected in both modules 30 such that timer circuit 74 in the respective units will each begin counting time to thereby allow for both local and remote display of duration as well, all based on the same transducer signals 24. Activation of either of switches 80 or switch 92 results in generating a reset signal which is communicated to both modules 30 to modify operation of circuitry 46 by causing reset of timer circuits 74 as a result of which displays 76 will both read zero.

Other types of circuit operation could be modified by a control signal other than a reset signal. By way of example, an auto-zero circuit or a verifier circuit, both of which are described in aforesaid application Ser. No. 07/932,645, could be provided in each of the modules 30 with the control signals being provided by switches (not shown), the poles of which are connected to further contacts in connectors 38 for communication between the units for both local and remote control. With the foregoing in mind, a third embodiment of a module configured for local and remote pressure display and circuit operation control is shown in FIG. 3.

Figure 3:
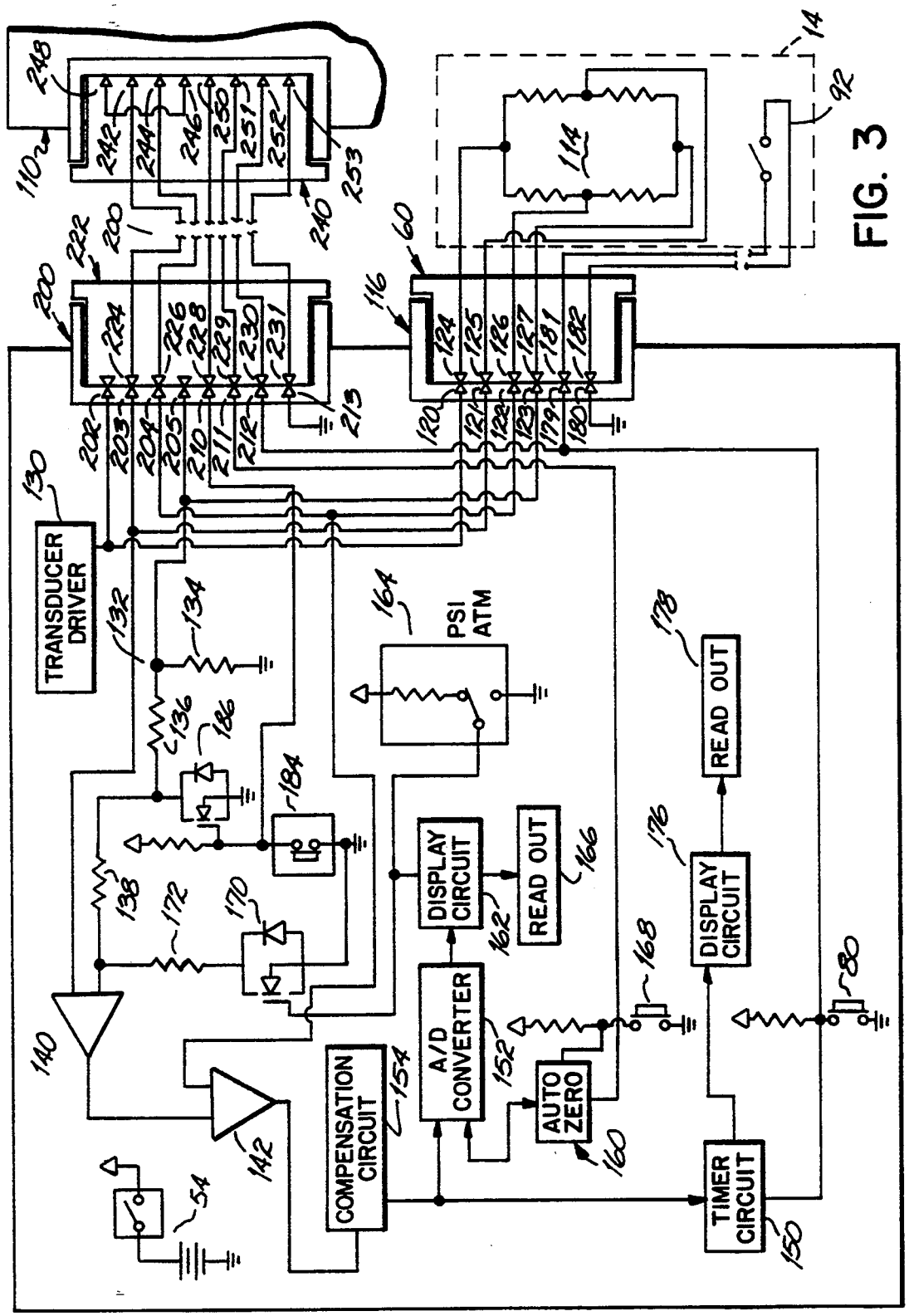
- FIG. 3 is a schematic diagram of a third embodiment of a pair of like modules interconnected for local and remote display of balloon catheter pressure and control of the modules in accordance with the principles of the present invention.

With reference to FIG. 3, monitor module 110 shown there is adapted to be interconnected to another like module 110 for local and remote display of balloon catheter pressure and control of the modules in accordance with the principles of the present invention. Module 110 includes circuitry 112 designed in part to work with a wheatstone bridge transducer 114 mounted on syringe housing 14. Transducer 114 may be part number SCC5008H available from Sensym, Inc. of Sunnyvale, Calif. Connector 116 of module 110 includes contacts 120, 121, 122 and 123 which interconnect to contacts 124, 125, 126 and 127, respectively, of connector 60 of cable 26 for communication of excitation signals and receiving differential transducer signals to and from transducer 114. To this end, contact 120 is coupled to transducer driver 130 such as a one (1) mA source of current. Connector 123, on the other hand, is the sink for that source and is connected to node 132, which is coupled to ground through 19.6 ohm resistor 134 and through 27.4 kilohm (Kohm) resistor 136 either to ground or through 20 Kohm resistor 138 to one input of differential amplifier 140 to provide a biasing level thereto and for purposes of utilizing the verifier circuit as will be described.

The differential transducer signals from transducer 114 are coupled through contacts 121 and 122, with contact 121 being wired to the other input of amplifier 140 to provide an output based on the difference between that signal and the reference level as established by the one mA transducer driver 130 through contacts 120 and 123 as above described. The output of amplifier 140 and the other transducer signal from contact 122 are coupled to the respective inputs of differential second amplifier 142 which, based on the difference therebetween, provides a single ended output which is coupled through compensation circuit 154 to timer circuit 150 and A/D converter 152. Although not shown, it will be readily appreciated that buffer amplifiers may be provided to buffer the inputs to amplifiers 140 and 142 and to provide a high impedance input to the transducer signals.

The single-ended output from amplifier 140 is compared by A/D converter 152 against a reference signal such as a signal from auto-zero circuit 160, so as to provide on the output of A/D converter 152 a signal representing a number correlated to the pressure in balloon 16. The output of A/D converter 152 is coupled to display circuit 162 which, depending upon the state of switch 164, will convert the output of A/D converter 152 to numbers which correspond to pressure in selected units of pressure such as either atmospheres or PSI, for example, which numbers are then coupled to read-out 166 for display of pressure in the selected units of pressure. Auto-zero circuit 160, which will be described below in greater detail, provides a reference level to A/D converter 152 such that, at ambient, the signals from transducer 114 will cause A/D converter 152 to output a signal to display circuit 162 such that read-out 166 displays zero atmospheres or zero PSI depending upon the state of switch 164. Auto-zero circuit is activated by providing an auto-zero signal from switch 168 the output of which is normally a logic high but goes to ground when switch 168 is activated. As will further be seen in FIG. 3, the signal from switch 164 is also coupled to the input of FET switch 170 to selectively couple the input of amplifier 140 to ground through 100 Kohm resistor 172 so as to offset the level difference seen by amplifier 140 for purposes to be described.

The signal from amplifier 142 is also coupled (via compensation circuit 154) to timer circuit 150 (like the circuit 140 shown in FIG. 8 of the aforementioned application Ser. No. 07/932,645) which, upon detecting an increase in the inflation pressure represented by an increase in the magnitude of the signal from amplifier 142, initiates a count which is provided to display circuit 176 so as to be converted to numbers for display on read-out 178 such that the duration of inflation may be determined. Timer circuit 150 may be reset to zero upon activation of reset switch 80 as described in connection with modules 30 of system 70 in FIG. 2. Alternatively, timer circuit 160 may respond to the reset signal generated by activation of switch 80 in a couple of different ways. If circuit 150 is already counting, the reset signal causes circuit 150 to stop counting and "freezes" the display at that time. If circuit 150 is not counting (e.g. it was stopped by a previous reset signal), the reset signal causes circuit 150 and, hence display 178, to reset to zero and then begin counting. Additionally, if timer circuit 150 is not already counting, increse in pressure as sensed from amplifier 142 resets the circuit to zero and circuit 150 begins counting time. Connector 116 is further provided with contacts 179 and 180 and connector 60 is provided with contacts 181 and 182 for interconnecting switch 92 on syringe housing 14 to the reset input of timer circuit 150 and to ground, respectively, such that timer circuit 150 may be reset by activation of switch 92 as well.

A further feature of module 110 is inclusion of a verifier circuit to cause a predetermined change in a reference level to amplifier 140 such that the pressure display readout 166 changes by a fixed amount if circuitry 112 is operating properly. Various verifier circuits are as described in significant detail in the aforesaid application Ser. No. 07/932,645 and need not be repeated here. The verifier circuit of module 110 includes a verifier switch 184, activation of which couples the input of FET switch 186 to ground to open same. When switch 186 is open, the voltage divider network on the input to amplifier 140 is changed causing a predetermined increase in the level difference between the two inputs to amplifier 140 such that the read-out of pressure at display 166 increments by a known, fixed amount if circuitry 112 is operating correctly. When switch 164 is in the position shown in FIG. 3 to cause display circuit 162 to produce numbers for display in PSI, the level difference to amplifier 140 is offset by the impact of resistor 172 coupled to ground such that activation of switch 184 will normally cause read-out 166 to increment by 100 PSI. In the ATM position of switch 164, the level difference does not include the effect of resister 172 such that read-out 166 will normally increment by 10 ATM. Although shown as a purely mechanical switch, switch 164 may be comprised of a mechanical switch which toggles a monostable multivibrator every time the switch is closed to ground, with the Q output of the monostable multivibrator being the output of switch 164 as seen in FIG. 3. The Q and $\bar{Q}$ outputs thereof may also drive a pair of LED's to indicate whether module 110 is in the PSI or ATM mode, respectively.

So that module 110 may be interconnected in a daisy-chain approach for both remote and local display and control, module 110 is further provided with a second connector 200 having contacts 202, 203, 204 and 205 wired in parallel with contacts 120, 121, 122, and 123, respectively, for communication of the excitation signals and transducer differential signals. Connector 200 is further provided with contact 210 for communicating the verifier signal, contact 211 for communicating the auto-zero signal, contact 212 for communicating the reset signal and contact 213 for communicating the ground signal to the other module 110. An interconnecting cable 220 is provided for interconnecting the connectors 200 of the two modules 110. At one end of the cable 220 is a connector 222 having contacts 224 and 226 for interconnecting with transducer signal contacts 203 and 204 for communicating the differential transducer signals between the units. Further contacts 228, 229, 230 and 231 are provided for interconnecting with contacts 210 through 213, respectively, for communicating the verifier, auto-zero, timer reset, and ground signals over cable 220. At the other end of cable 220 is another connector 240 having contacts 242 and 244 interconnected with contacts 224 and 226 of connector 222 for communicating the transducer signals. Another pair of contacts 246 and 248 are provided in connector 240 and they are jumpered together such that the one mA transducer driver signal from driver 130 of the second module 110 is coupled back to node 132 and amplifier 140 of that unit to provide the level reference for purposes of processing and verification as above-described. Thus, the excitation signals from one of modules 110 are not in fact shared with the other module 110. Connector 240 is otherwise provided with additional contacts 250, 251, 252 and 253 which interconnect with contacts 228 through 231 and thus to contacts 210 through 213 for communicating the verifier, auto-zero, reset and ground signals as before described.

Figure 4:
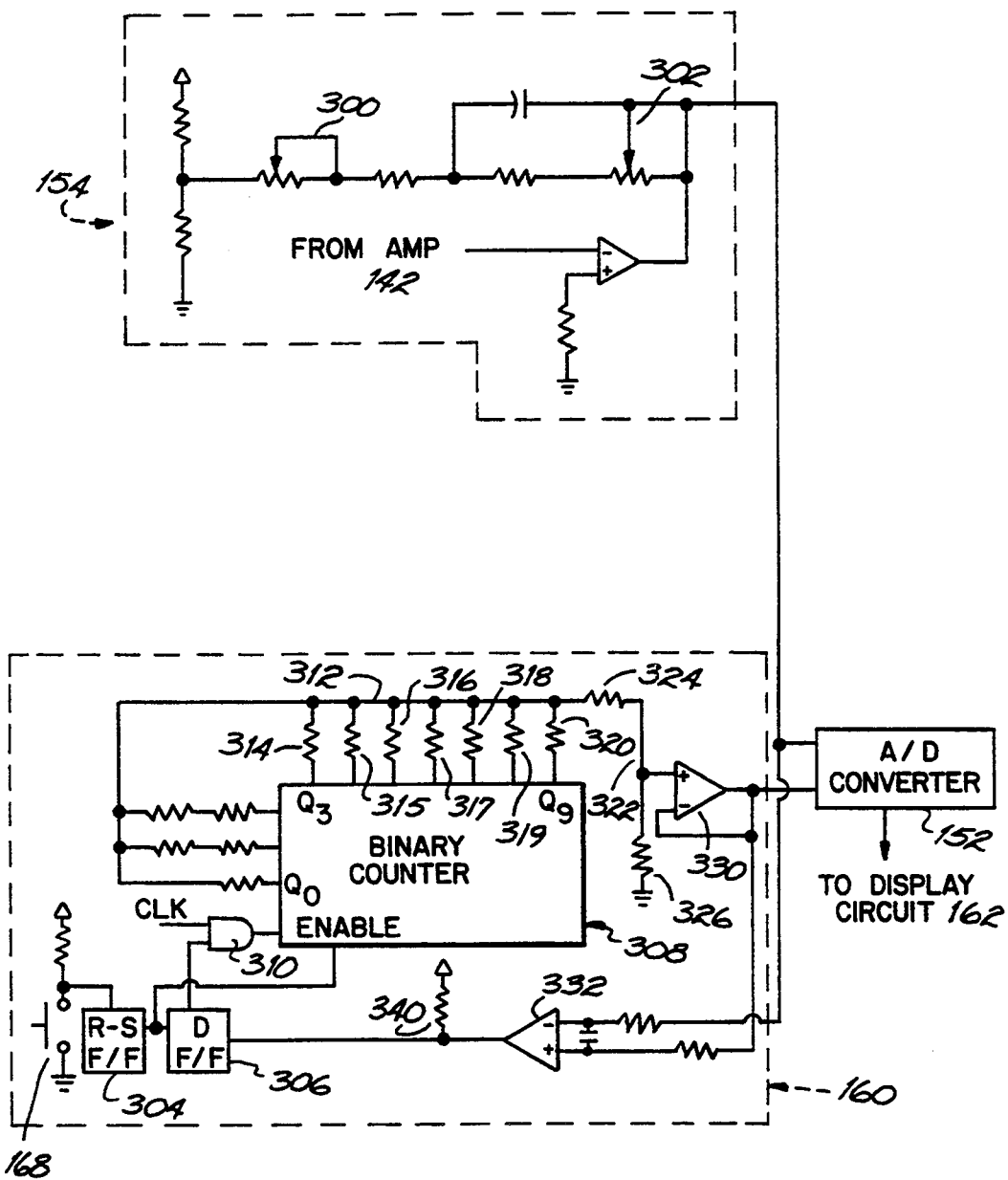
FIG. 4 is a schematic diagram of the auto-zero and compensation circuitry of FIG. 3.

As shown in greater detail in FIG. 4, the output of differential amplifier 142 is compensated through a compensation circuit 154 that adjusts the electrical transducer signals to the desired operational range. Potentiometers 300, 302 are adjusted at the point of assembly by using a signal emulating the transducer signals from a transducer calibrated in accordance with its manufacturer's specifications. With respect to the auto-zero circuit 160, activation of auto-zero switch 168 selectively couples electrical ground to the set input of R-S flip-flop 304. The Q output of flip-flop 304 is coupled to the input of D flip-flop 306 and to an enable input of binary counter 308. The Q output of D flip-flop 306 is coupled to one input of dual input AND gate 310 that has its other input tied to a clock signal, which is, for example, 2048 Hz. Outputs $Q_0$–$Q_9$ are tied to a common point 312 through respective resistors 314–320. Resistors 314–320 have values of 499 Kohm, 249 Kohm, 124 Kohm, 61.9 Kohm, 30.9 Kohm, 15.4 Kohm and 7.6 Kohm, respectively. Common point 312 supplies a signal level to voltage divider 322 comprised of 10 Kohm resistor 324 and 1.21 Kohm resistor 326. Voltage divider 322 drives the non-inverting input of operational amplifier 330. The output of amplifier 330 is coupled to the reference input of A/D converter 152 and back to the inverting input of amplifier 330. The output amplifier 330 is also coupled to an input of comparator 332 having its other input coupled to the signal from compensation circuit 154. The output of comparator 332 is tied to the power supply from battery 54 through pull-up resistor 340 and to the reset input of D flip-flop 306.

When auto-zero switch 168 is activated to couple electrical ground to the set input of R-S flip-flop 304, the Q output thereof goes to a logic high state which enables binary counter 308 to count pulses and also transitions the input of D flip-flop 306 to set the Q output thereof to a logic high. The logic high on the Q output of flip-flop 306 enables AND gate 310 to couple clock pulses on its other input to binary counter 308. Counter 308 provides a sequential binary count on its outputs $Q_0$–$Q_9$ in response to the input of the clock signals from AND gate 310. The binary count on outputs $Q_0$–$Q_9$ selectively varies the signal level and corresponding signal level at common point 312. As the signal at common point 312 varies so does the output of voltage divider 322 that is coupled through operational amplifier 330 to the reference input of A/D converter 152.

As long as the signal corresponding to the varying electrical signal from binary counter 308 is less than the output from compensation circuit 154, the output of the comparator 332 remains a logic low. When the varying signal from binary counter 308 is slightly greater than the output of circuit 154, the output of the comparator goes to a logic high to reset D flip-flop 306. Resetting the D flip-flop causes its Q output to go low which disables AND gate 310 from passing the clock pulses through to counter 308. Thus, outputs $Q_0$–$Q_9$ of counter 308 remain at the state corresponding to the last counted pulse and the signal at common point 312 and voltage divider 322 remain unchanged. Correspondingly, the output of operational amplifier 330 remains unchanged so the reference signal to the reference input of A/D converter 152 is established.

When catheter 18 is vented to the room pressure and auto-zero switch 168 is depressed, operation of auto-zero circuit 160 causes the signal at the A/D converter 152 reference input to reach a value where it equals the transducer signals to be converted. Because the difference between the reference input and the transducer signals is zero, the digital value from A/D converter 152 is displayed as a numerical pressure value of zero on the digital read-out 166. Thus, the reference signal from auto-zero circuit 160 is set to a value corresponding to the ambient pressure in the room plus any transducer offset voltage. By releasing switch 168 and closing catheter 18 from the room pressure, balloon pressure is measured with reference to the ambient pressure in the room which corresponds to a numerical read-out of zero atmospheres or PSI.

Figure 5:
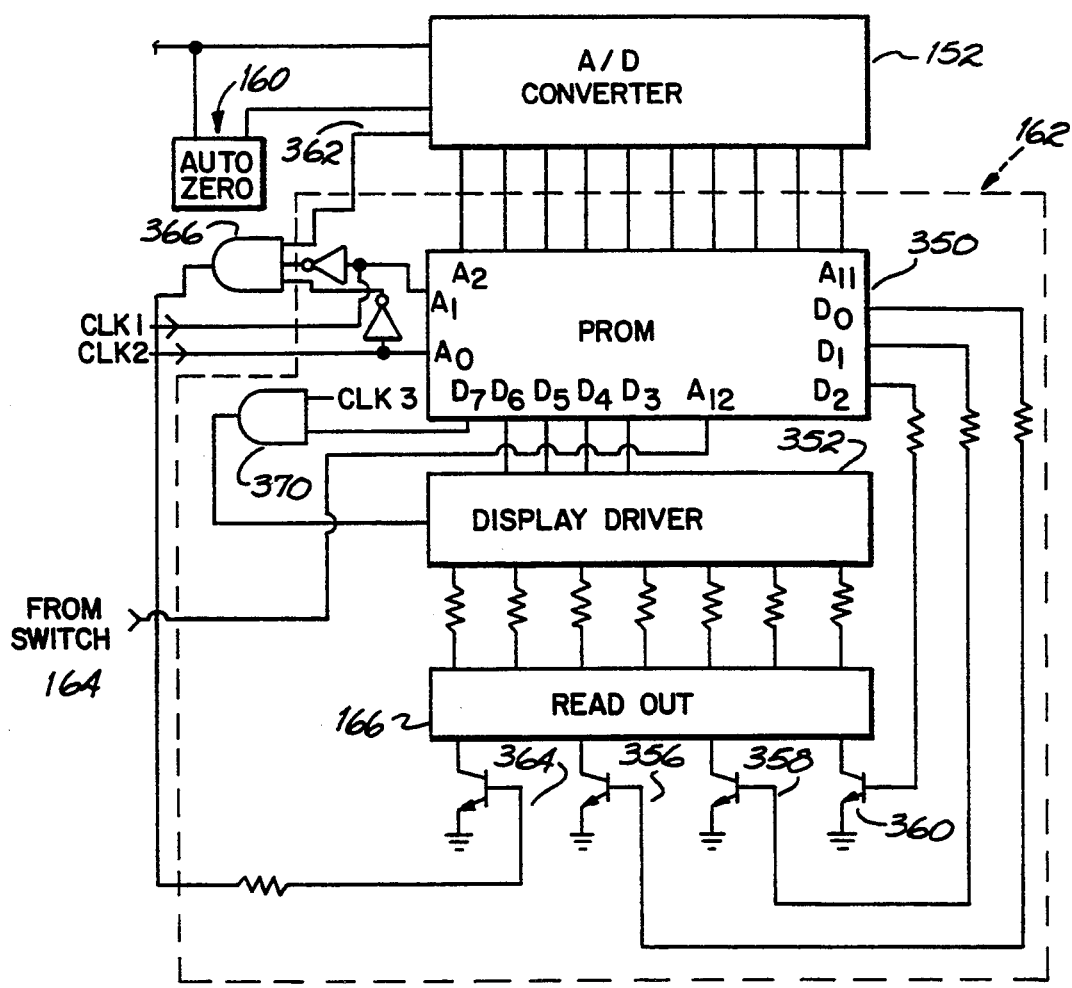
FIG. 5 is a schematic diagram of the display circuitry of FIG. 3.

Display circuitry 162 is shown in FIG. 5 and includes a programmable read-only memory (PROM) 350 and segment display driver 352 to drive digital read-out 166. digital read-out 166 may have three segmented digits and a sign segment. Address lines $A_2$–$A_{11}$ of PROM 350 are coupled to the digital outputs of A/D converter 152, the two least significant address bits $A_0$, $A_1$, are coupled to clock signals CLK1 (2048 Hz), CLK2 (1024 Hz), and most significant bit $A_{12}$ is coupled to switch 164. Four of the data outputs, $D_3$–$D_6$, of the PROM 350 are coupled to segment display driver 352. The data from PROM 350 on these four outputs correspond to the binary-coded decimal (BCD) digits to be displayed on read-out 166. Data outputs $D_0$, $D_1$, $D_2$ are coupled through 7.5 Kohm resistors to the base of three bipolar transistors 356, 358, 360, respectively. These transistors are used to select the digit in digital read-out 166 to be illuminated. A polarity output 362 of A/D converter 152 is coupled to a fourth bipolar transistor 364 through triple input AND gate 366 to control the sign segment of read-out 166. All of the collectors of transistors 356, 358, 360 and 364 are coupled to digital read-out 166 and the emitters of the transistors are coupled to electrical ground.

To display pressure data, the digital output of A/D converter 152 and the two clock signals coupled to the least significant address bits define an address and the data stored at the address is output to display driver 352 and transistors 356, 358 and 360. Of the three data outputs $D_0$, $D_1$, $D_2$ coupled to these transistors, only one is logically active at a time to forward bias the base-emitter junction of one of the transistors which selects the segments of one digit in read-out 166 for illumination. The segments of the selected digit are illuminated in accordance with the segment driving signals from display driver 352 which were derived from the four BCD data outputs on $D_3$–$D_6$ from PROM 350. As the two least significant bits of the address lines $A_0$, $A_1$ of the PROM 350 change in accordance with clock signals CLK1 and CLK2, the selected memory locations corresponding to the data on address lines $A_0$–$A_1$ provide BCD data on $D_3$–$D_6$ for each of the digits and the proper control bits on $D_0$–$D_2$ to select the corresponding digit for the pressure sensed in the balloon for illumination by read-out 166. The sign segment of read-out 166 is driven by the polarity bit 362 from A/D converter 152 which is either a blank or minus sign. The clock signals coupled to the other two inputs of the AND gate 366 are used to "blink" the minus sign when it is activated.

The most significant bit $D_7$ of the data stored within the PROM may be a logic low for pressure values within the normal operational range of module 110 which is, for example, −1 atmosphere to +30 atmospheres. When the pressure exceeds the upper limit of this range, data stored in PROM 350 corresponding to these higher pressures drives the most significant data bit $D_7$ output by PROM 350 to a logic high. This bit is coupled to a dual input AND gate 370 which has its remaining input tied to a clock signal CLK3, which may be 2 Hz. The output of gate 370 is coupled to the blanking input of display driver 352 so the pressure read-out provides a blinking indication of the pressure sensed above about 30 atmospheres.

The state of switch 164 dictates whether the atmosphere or PSI units of pressure are selected. Thus, in the atmosphere position of switch 164, the proper page of PROM 350 is selected to output numbers in units of atmospheres corresponding to the magnitude of the output of converter 152. Similarly, with switch 164 in the PSI position as shown in FIG. 3, another page of PROM 350 is selected to produce numbers in units of PSI corresponding to the magnitude of the output of converter 152.

In use of modules 110 of FIG. 3, connector 60 of cable 26 is plugged into connector 116 of one module 110 so as to interconnect the respective contacts thereof. Cable 220 is utilized with connector 222 plugged into connector 200 of module 110 having connector 60 received in its connector 116 and connector 240 of cable 220 plugged in to the connector 200 of the remote module 110. Before actually inflating balloon 16, catheter 18 is vented to atmosphere such as by opening a stopcock (not shown) coupled between outlet 20 and balloon catheter 18. Auto-zero switch 168 is activated in either of modules 110 to cause both auto-zero circuits 160 of the two modules to generate a level signal for use by A/D converter 152 such that read-outs 166 will both display zero at that time. Thereafter, the stopcock (not shown) is closed and inflation may take place. As balloon 16 is inflated, transducer signals are communicated through contacts 125 and 126 of connector 60 to contacts 121 and 122 and 204 and 205 within module 110 as well as to circuitry 112 as before described. The signals are further communicated through cable 220 to remote unit 110. As a result, there is simultaneous processing and display of pressure in read-out 166 of the respective units. Additionally, the onset of inflation pressure is detected in both modules 110 such that timer circuit 150 in each of the respective units will begin counting time to thereby allow for both local and remote display of duration as well, all based on the same transducer signals. At any time during use of modules 110, the verifier switch 184 may be activated on either of modules 110 causing a verifier signal to be coupled to FET switch 186 of that unit and also through cable 220 to a similar FET switch 186 of the other unit thereby causing both units to have a change in their level inputs to amplifiers 140 such that verification of circuitry 112 in both units may take place. In this event, the read-outs 166 should both change by respective fixed amounts although it will be appreciated that one of modules 110 could be set to display in ATM while the other could be set to display in PSI such that one display is incremented by ten and the other by one hundred, respectively. Activation of either of switches 80 in either unit 110 or switch 92 on syringe housing 14 results in generating a reset signal which is communicated to both modules 110 to modify operation of circuitry 112 by causing reset of timer circuits 150 as before described.

As will be appreciated, activation of any of verifier switches 184, auto-zero switches 168, or reset switches 80, or switch 92 causes a modification to the operation of circuitry 112 as above described. In this regard, the output of any of those switches is a control signal which causes such operational modification. As will further be appreciated, although only switch 92 is shown on the syringe housing 14, one or more further switches could be provided in addition to, or in lieu of, switch 92 so as to provide auto-zero and verification control from the syringe housing as will be well understood by those skilled in the art.

Modules 110 may also be operated under battery power (battery 54) and a circuit provided which monitors the battery voltage level. When the battery level falls below a predetermined level that indicates the battery may be failing, a low battery LED (not shown) is illuminated to alert the operator to the low battery condition. Additionally, or alternatively, readout 166 may be forced to read all 8's.

While the present invention has been illustrated by the description of alternative embodiments, and while the embodiments have been described in considerable detail, it is not the intention of the applicant to restrict or in any way limit the scope of the appended claims to such detail. Additional advantages and modifications will readily appear to those skilled in the art. For example, circuitry could be provided as described in aforesaid application Ser. No. 07/932,645 to provide an audible indication that the balloon is deflated. Also, the pressure and duration readouts could be part of one display rather than two separate displays as shown. The invention in its broadest aspects is therefore not limited to the specific details, representative apparatus and method, and illustrative examples shown and described. Accordingly, departures may be made from such details without departing from the spirit or scope of applicant's general inventive concept.

What is claimed is:

1. A balloon catheter pressure monitoring module adapted for remote and local display of pressure in a balloon catheter comprising:
    circuit means for processing a transducer signal communicated from a pressure transducer in fluid communication with the balloon catheter, the circuit means including display means for displaying pressure corresponding to the communicated transducer signals; and
    first and second connector means each for connecting to respective cables, each connector means having first contact means for communicating transducer signals, respective first contact means of each connector means being coupled to one another and to the circuit means such that a first cable coupled to a pressure transducer generating a transducer signal may be plugged into the first connector means to communicate the transducer signal to the circuit means for local display of pressure, and such that a second cable may be plugged into the second connector means to communicate the transducer signal to a remote pressure monitoring module for remote display of pressure corresponding to the transducer signal.

2. The pressure monitoring module of claim 1 wherein the circuit means includes timer means for determining duration of pressurization of the balloon catheter, the display means further for displaying the duration, the timer means being reset in response to a reset signal, the second connector means further having second contact means coupled to the circuit means for communicating a reset signal such that the reset signal for resetting the timer means will also be communicated through the second cable to the remote pressure monitoring module.

3. The pressure monitoring module of claim 2 further comprising switch means communicating with the circuit means for generating the reset signal.

4. The pressure monitoring module of claim 2, the first connector means further having second contact means coupled to the circuit means and the second contact means of the second connector means for communicating a reset signal such that the reset signal may be provided via the first cable.

5. The pressure monitoring module of claim 4 further comprising the first cable and, coupled to the cable, switch means for generating the reset signal.

6. The pressure monitoring module of claim 1 wherein the circuit means includes control means for modifying operation of the circuit means when the control means is activated, the control means being activated in response to a control signal, the second connector means further having second contact means coupled to the circuit means for communicating a control signal such that the control signal for activating the circuit means will also be communicated through the second cable to the remote pressure monitoring module.

7. The pressure monitoring module of claim 6 further comprising switch means communicating with the circuit means for generating the control signal.

8. The pressure monitoring module of claim 6, the first connector means further having second contact means coupled to the circuit means and the second contact means of the second connector means for communicating a control signal such that the control signal may be provided via the first cable.

9. The pressure monitoring module of claim 8 further comprising the first cable and, coupled to the cable, switch means for generating the control signal.

10. The pressure monitoring module of claim 6 wherein the control means includes verifier means for verifying operation of the circuit means when activated by the control means such that the display means displays a pressure offset by a known amount when the circuit means is operating properly.

11. The pressure monitoring module of claim 6 wherein the control means includes auto-zero means for zeroing the circuit means such that the display means reads zero at ambient pressure when the control means is activated.

12. In combination, local and remote balloon catheter pressure monitoring modules each adapted for display of pressure in a balloon catheter, each pressure monitoring module comprising:
    circuit means for processing a transducer signal communicated from a pressure transducer in fluid communication with the balloon catheter, the circuit means including display means for displaying pressure corresponding to the communicated transducer signals; and
    first and second connector means for connecting to a first cable and a second cable, respectively, each connector means having first contact means for communicating transducer signals, respective first contact means of each connector means being coupled to one another and to the circuit means such that a first cable coupled to a pressure transducer generating a transducer signal may be plugged into the first connector means to communicate the transducer signal to the circuit means for local display of pressure, and such that a second cable may be plugged into the second connector means to communicate the transducer signal to the second connector means of the other pressure monitoring module for remote display of pressure corresponding to the transducer signal.

13. The pressure monitoring modules of claim 12 wherein each of the circuit means includes timer means for determining duration of pressurization of the balloon catheter, the respective display means further for displaying the duration, the timer means being reset in response to a reset signal, the second connector means further having second contact means coupled to the circuit means for communicating a reset signal such that the reset signal from one of the modules will also be communicated through the second cable to the other of the modules.

14. The pressure monitoring modules of claim 13 each further comprising switch means communicating with the respective circuit means for generating the reset signal.

15. The pressure monitoring modules of claim 13, the first connector means further having second contact means coupled to the circuit means and the second contact means of the second connector means for communicating a reset signal such that the reset signal may be provided via the first cable.

16. The pressure monitoring modules of claim 15, further comprising the first cable and, coupled to the cable, switch means for generating the reset signal.

17. The pressure monitoring modules of claim 12 wherein each of the circuit means includes control means for modifying operation of the respective circuit means when the control means is activated, the control means being activated in response to a control signal, the second connector means further having second contact means coupled to the circuit means for communicating a control signal such that the control signal for activating the circuit means from one of the modules will also be communicated through the second cable to the other of the modules.

18. The pressure monitoring modules of claim 17, each further comprising switch means communicating with the respective circuit means for generating the control signal.

19. The pressure monitoring modules of claim 17, the first connector means each further having second contact means coupled to the circuit means and the second contact means of the second connector means for communicating a control signal such that the control signal may be provided via the first cable.

20. The pressure monitoring module of claim 19 further comprising the first cable and, coupled to the cable, switch means for generating the control signal.

21. The pressure monitoring modules of claim 17 wherein each of the control means includes verifier means for verifying operation of the respective circuit means when actuated by the control signal such that the respective display means displays a pressure offset by a known amount when the respective circuit means is operating properly.

22. The pressure monitoring modules of claim 17 wherein each of the control means includes auto-zero means for zeroing the respective circuit means when the control means is activated such that the respective display means reads zero at ambient pressure.

23. The pressure monitoring modules of claim 12 wherein each of the circuit means includes means for converting the transducer signal to pressure in selected units of pressure and means for selecting the units of pressure, the respective display means displaying pressure in the selected units of pressure whereby pressure may be displayed simultaneously in different units of pressure on the respective modules.

24. The pressure monitor modules of claim 23 wherein the respective means for converting the transducer signal to pressure includes means for converting the transducer signal to pressure in units of one of PSI and atmospheres.

25. The pressure monitor modules of claim 12 further comprising the second cable interconnecting the second connector means of the modules.

* * * * *